US011148993B1

United States Patent
Wei et al.

(10) Patent No.: US 11,148,993 B1
(45) Date of Patent: Oct. 19, 2021

(54) METHOD FOR PURIFYING POLYUNSATURATED FATTY ACID BY USING CONTINUOUS REACTOR

(71) Applicant: Chunghwa Chemical Synthesis & Biotech Co. Ltd., New Taipei (TW)

(72) Inventors: Ching-Peng Wei, New Taipei (TW); Yen-Shih Tung, New Taipei (TW); Tzu-Ai Lee, New Taipei (TW); Jenn-Line Sheu, New Taipei (TW)

(73) Assignee: CHUNGHWA CHEMICAL SYNTHESIS & BIOTECH CO. LTD., New Taipei (TW)

(*) Notice: Subject to any disclaimer, the term of this patent is extended or adjusted under 35 U.S.C. 154(b) by 0 days.

(21) Appl. No.: 16/996,288

(22) Filed: Aug. 18, 2020

(30) Foreign Application Priority Data

Jun. 5, 2020 (TW) ................................. 109118986

(51) Int. Cl.
*C07C 67/62* (2006.01)
*C11B 3/00* (2006.01)
*C07C 69/587* (2006.01)

(52) U.S. Cl.
CPC ............ *C07C 67/62* (2013.01); *C07C 69/587* (2013.01); *C11B 3/001* (2013.01); *C11B 3/006* (2013.01)

(58) Field of Classification Search
CPC ....... C07C 67/62; C07C 69/587; C11B 3/001; C11B 3/006; C11B 5/0042; C11C 1/08
See application file for complete search history.

(56) References Cited

U.S. PATENT DOCUMENTS

| 5,189,189 A * | 2/1993 | Misawa | C07C 67/60 554/194 |
| 9,145,533 B2 * | 9/2015 | Breivik | C11B 3/006 |
| 9,365,800 B2 * | 6/2016 | Harata | C11C 1/007 |
| 2018/0148664 A1 * | 5/2018 | Tabata | C07C 67/58 |
| 2018/0155268 A1 * | 6/2018 | Mankura | C07C 69/58 |
| 2020/0172829 A1 * | 6/2020 | Ikemoto | C11C 1/005 |

FOREIGN PATENT DOCUMENTS

WO    WO-2018230622 A1 * 12/2018 ........... C11B 7/0025

* cited by examiner

*Primary Examiner* — Yate' K Cutliff
(74) *Attorney, Agent, or Firm* — Muncy, Geissler, Olds & Lowe, P.C.

(57) ABSTRACT

The present invention relates to a method for purifying polyunsaturated fatty acid using a continuous reactor, and the method comprises: (a) complexing step, (b) cleaning step, (c) extracting step, and (d) concentrating and drying step. The method of the present invention reacts a polyunsaturated fatty acid and a silver salt aqueous solution in a continuous reactor to form a complex of the polyunsaturated fatty acid and silver, and then cleans the complex with a first organic solvent to improve the purity of the complex; afterwards, a second organic solvent is used to extract the purified polyunsaturated fatty acid. The method of the present invention can continuously produce polyunsaturated fatty acids with high yield and high purity.

28 Claims, 2 Drawing Sheets

METHOD FOR PURIFYING POLYUNSATURATED FATTY ACID BY USING CONTINUOUS REACTOR

BACKGROUND OF THE INVENTION

1. Technical Field

The present invention relates to a method for purifying a polyunsaturated fatty acid using a continuous reactor and more particularly to a method for purifying a polyunsaturated fatty acid by complexing the polyunsaturated fatty acid with a silver salt aqueous solution in a continuous reactor.

2. Description of Related Art

The molecules of a long-chain fatty acid, e.g. polyunsaturated fatty acid (PUFA), and its derivatives are very important for the operation of human body and have been used as raw material for health foods and pharmaceuticals, and the commonly found polyunsaturated fatty acid includes docosahexaenoic acid (DHA), docosapentaenoic acid (DPA) and eicosapentaenoic acid (EPA).

There is at least one double bond in the molecule of polyunsaturated fatty acids, and the polyunsaturated fatty acids can be classified into linoleic acid, α-linolenic acid, oleic acid and palmitoleic acid according to their parent fatty acid. Mammals cannot synthesize linoleic acid and α-linolenic acid, which are essential fatty acids (EFAs) and must be ingested from the daily diet. From a medical point of view, a polyunsaturated fatty acid can reduce low-density lipoprotein cholesterol (commonly known as bad cholesterol, LDL), increase high-density lipoprotein cholesterol (commonly known as good cholesterol, HDL), maintain body functions and reduce cell aging. In addition, a polyunsaturated fatty acid can also treat cancers or skin diseases, etc., and play an important role in cardiovascular diseases and inhibiting tumor cell proliferation.

BRIEF SUMMARY OF THE INVENTION

Polyunsaturated fatty acids are easily oxidized and unstable in general environment and prone to isomerization, oligomerization or peroxidation. Accordingly, it is not easy to separate and purify a polyunsaturated fatty acid but easy to make it degraded or decomposed. Therefore, the present invention intends to provide a method for purifying a polyunsaturated fatty acid by using a continuous reactor, which can continuously purify a polyunsaturated fatty acid so as to improve its yield and purity and can recycle a solvent, a cleaned polyunsaturated fatty acid and a silver salt aqueous solution in a process so as to facilitate the purification of the polyunsaturated fatty acid and its application as raw material for health foods and pharmaceuticals.

The objective of the present invention is to provide a method for purifying polyunsaturated fatty acid using a continuous reactor, which includes a mixing unit and an extracting and separating unit, and the method comprising: (a) complexing step: reacting a polyunsaturated fatty acid and a silver salt aqueous solution in the mixing unit, and using the extracting and separating unit to separate a first aqueous layer and an oil layer; (b) cleaning step: reacting the first aqueous layer and a first organic solvent in the mixing unit, and using the extracting and separating unit to separate a second aqueous layer and a first organic layer; (c) extracting step: reacting the second aqueous layer and a second organic solvent in the mixing unit, and using the extracting and separating unit to separate a third aqueous layer and a second organic layer; and (d) concentrating and drying step: concentrating and drying the second organic layer to obtain a purified polyunsaturated fatty acid.

Another objective of the present invention is to provide a method for purifying polyunsaturated fatty acid using a continuous reactor, which includes a plurality of mixing units and an extracting and separating unit, and the method comprising: (a) complexing step: using the mixing unit to react a polyunsaturated fatty acid and a silver salt aqueous solution, and using the extracting and separating unit to separate a first aqueous layer and an oil layer; (b) cleaning step: using the plurality of mixing units to feed a first organic solvent in stages, reacting the first aqueous layer and the first organic solvent, and using the extracting and separating unit to separate a second aqueous layer and a first organic layer; (c) extracting step: using the plurality of mixing units to feed a second organic solvent in stages, reacting the second aqueous layer and the second organic solvent, and using the extracting and separating unit to separate a third aqueous layer and a second organic layer; and (d) concentrating and drying step: concentrating and drying the second organic layer to obtain a purified polyunsaturated fatty acid.

In a preferred embodiment, the polyunsaturated fatty acid in the complexing step (a) is added with a first organic solvent, and the weight ratio of the first organic solvent and the polyunsaturated fatty acid is 1:20 to 1:1. More preferably, the first organic solvent is n-heptane.

In a preferred embodiment, the second aqueous layer is diluted with pure water before the extracting step (c).

In a preferred embodiment, the second organic layer is further cleaned with water and saturated saline before being concentrated in the step (d).

In a preferred embodiment, the second organic layer is further added with activated carbon, stirred and filtered after being concentrated and before being dried in the step (d).

In a preferred embodiment, the polyunsaturated fatty acid comprises eicosatetraenoic acid (ETA), eicosatetraenoic acid ethyl ester, eicosapentaenoic acid (EPA), eicosapentaenoic acid ethyl ester (EPAE), heneicosapentaenoic acid (HPA), heneicosapentaenoic acid ethyl ester, docosapentaenoic acid (DPA), docosapentaenoic acid ethyl ester, docosahexaenoic acid (DHA), docosahexaenoic acid ethyl ester (DHAEE), tetracosapentaenoic acid, tetracosapentaenoic acid ethyl ester, nisinic acid or nisinic acid ethyl ester.

In a preferred embodiment, the purity of the polyunsaturated fatty acid is 60% or more.

In a preferred embodiment, the concentration of the silver salt aqueous solution is 40 to 70 wt %.

In a preferred embodiment, the first organic solvent and the second organic solvent include hexane, cyclohexane, heptane, n-heptane, toluene, ethyl acetate, ethyl isopropionate, xylene, ethylbenzene, methylene chloride, methyl tert-butyl ether, tetrahydrofuran (THF), 2-methyltetrahydrofuran, ethyl ether, dipropyl ether or isopropyl ether.

In a preferred embodiment, the first organic solvent is heptane or n-heptane.

In a preferred embodiment, the second organic solvent is toluene, heptane or n-heptane.

In a preferred embodiment, the mixing unit is a micro flow channel mixer.

In a preferred embodiment, the method is performed under light avoidance and inert gas conditions.

DETAILED DESCRIPTION OF THE INVENTION

The following embodiments should not be regarded as excessively limiting the present invention. Those with ordinary knowledge in the technical field of the present invention can make modification and variation to the embodiments discussed herein without departing from the spirit or scope of the invention, and the modification and variation still fall within the scope of the invention.

As used herein, the terms "a" and "an" refer to one or to more than one (i.e., to at least one) of the grammatical object of the article.

The method for purifying a polyunsaturated fatty acid by using a continuous reactor according to the present invention comprises, in sequence, a complexing step (a), a cleaning step (b), an extracting step (c) and a concentrating and drying step (d). Except for the concentrating and drying step (d), the remaining steps are carried out in a mixing unit and an extracting and separating unit of the continuous reactor. The complexing step (a) is performed to make a polyunsaturated fatty acid react with a silver salt aqueous solution so as to form a complex of hydrophilic unsaturated fatty acid and silver, and the complexing reaction will form an upper oil layer and a lower aqueous layer that will then be separated, wherein the lower aqueous layer is a first aqueous layer containing a complex of polyunsaturated fatty acid and silver, such as $Ag^+EPAE$ complex. The cleaning step (b) is performed to use a first organic solvent to clean the first aqueous layer so as to improve the purity of the complex; and after the first aqueous layer is cleaned, an upper organic layer and a lower aqueous layer will be formed and then be separated, wherein the upper organic layer and the lower aqueous layer are a first organic layer and a second aqueous layer respectively, the first organic layer has the first organic solvent, which can be directly recycled in a process, and the second aqueous layer contains the complex cleaned by the first organic solvent. The step (c) is performed to use a second organic solvent to extract the purified polyunsaturated fatty acid, that is, to make the second aqueous layer reacted with the second organic solvent; and after the purified polyunsaturated fatty acid is extracted, an upper organic layer and a lower aqueous layer will be formed and then be separated, wherein the upper organic layer and the lower aqueous layer are a second organic layer and a third aqueous layer respectively, the second organic layer contains the purified polyunsaturated fatty acid, and the third aqueous layer contains uncomplexed silver ions and silver salt aqueous solution that can be directly recycled. Finally, the concentrating and drying step (d) is performed to concentrate and dry the purified polyunsaturated fatty acid extracted by the second organic layer so as to obtain a solid purified polyunsaturated fatty acid, and the second organic solvent remaining in the second organic layer after the extracting step can be directly recycled and used in a process.

Figure 1:
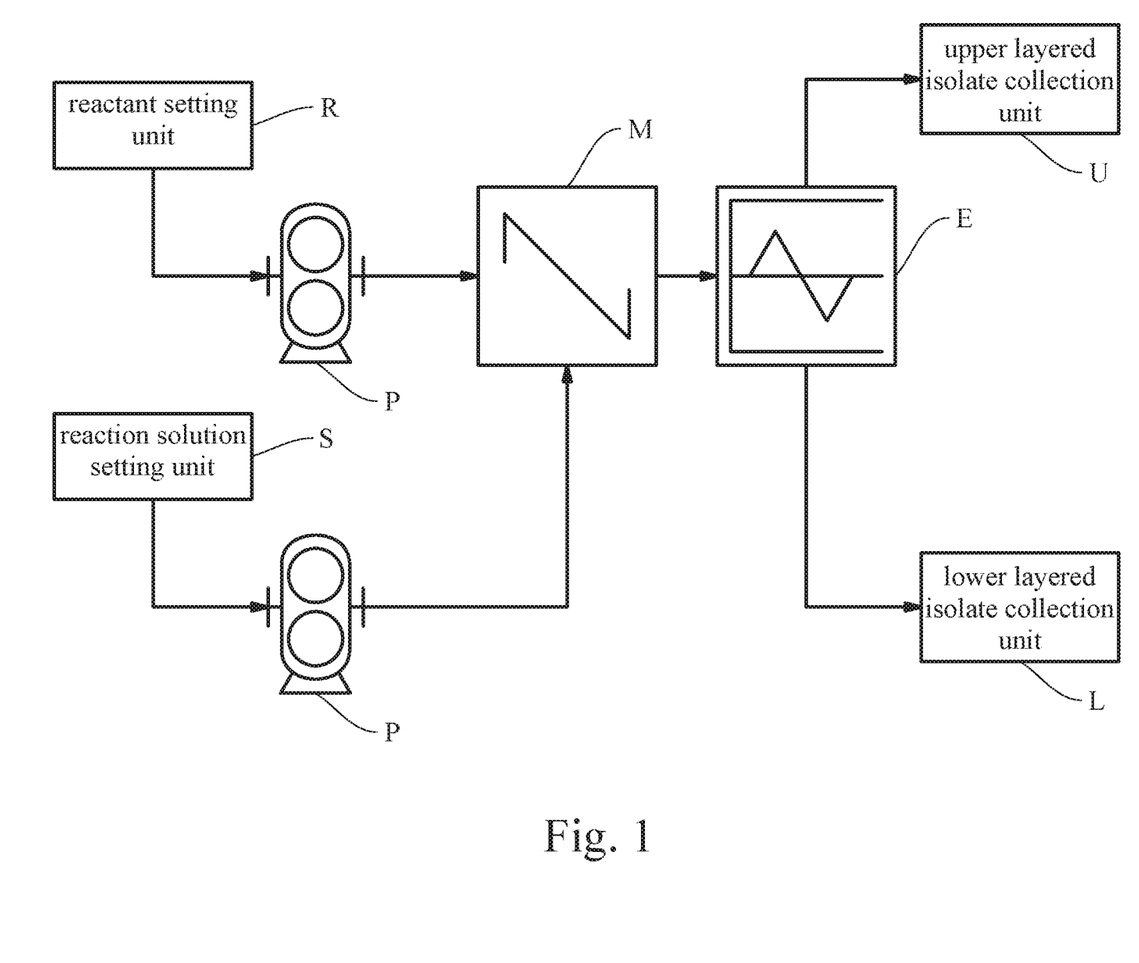
FIG. 1 is a schematic diagram of a first type of the continuous reactor of the present invention.
Figure 2:
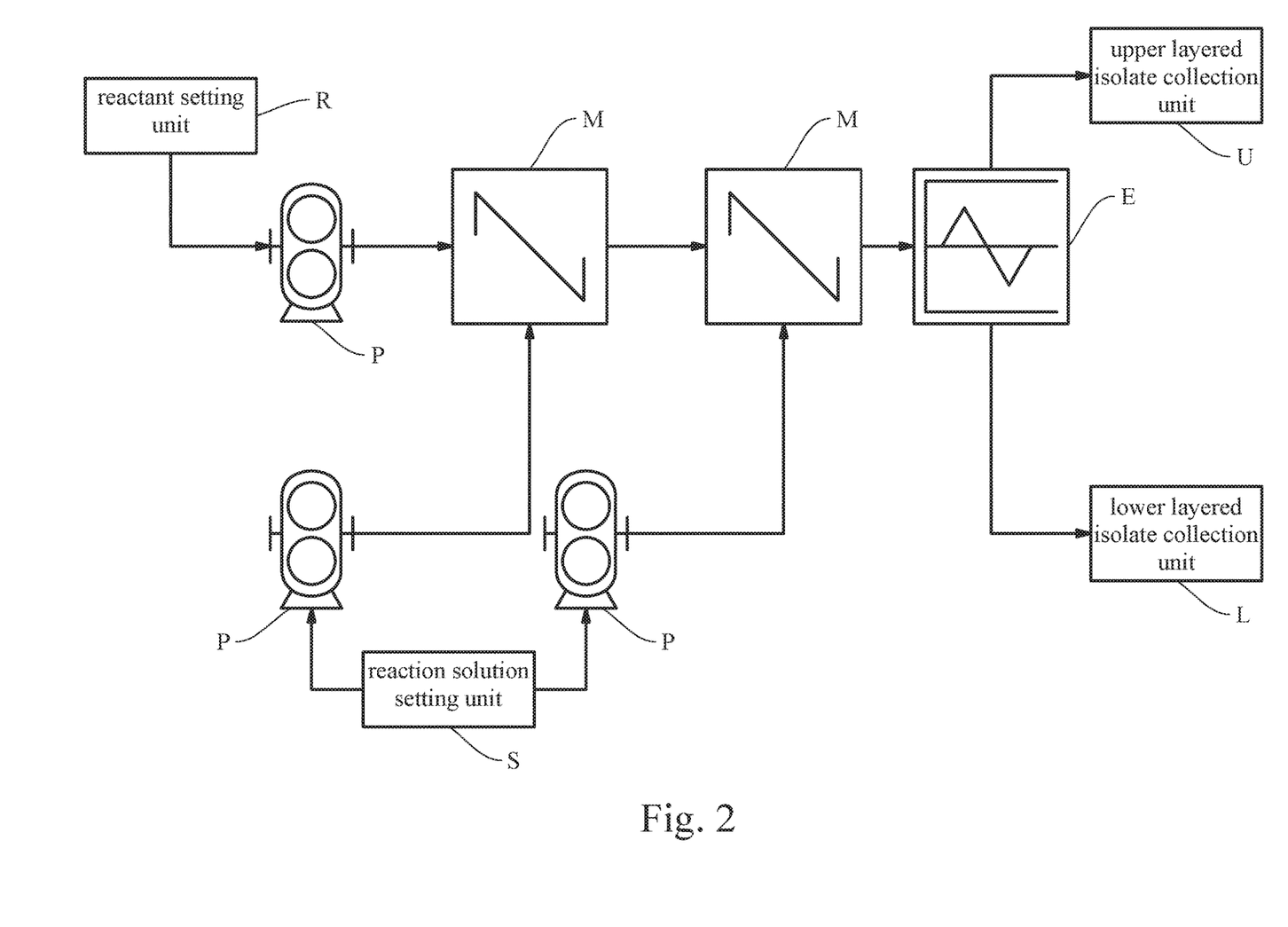
FIG. 2 is a schematic diagram of a second type of the continuous reactor of the present invention.

There are two types of continuous reactors. As shown in FIG. 1, the first type of continuous reactor includes a reactant setting unit R, a reaction solution setting unit S, a mixing unit M, an extracting and separating unit E, an upper layered isolate collection unit U and a lower layered isolate collection unit L. The reactant setting unit R is configured to set a reactant, and the reaction solution setting unit S is configured to set a reaction solution (that is, the solution that react with the reactant, i.e., the silver salt aqueous solution, the first organic solvent and the second organic solvent); and the reactant and the reaction solution are transported by a pump P to the mixing unit M for being mixed, and then separated through the extracting and separating unit E. The method of the present invention is to separate a mixture into an aqueous layer and an oil layer or into an aqueous layer and an organic layer. The aqueous layer is heavier than the oil layer and the organic layer. When the layers are separated, the aqueous layer is located in the lower layer while the oil layer and the organic layer are located in the upper layer. Therefore, the extracting and separating unit E will separate the aqueous layer to the lower layered isolate collection unit L and separate the oil layer and the organic layer to the upper layered isolate collection unit U. Further, as shown in FIG. 2, the second type of continuous reactor includes a reactant setting unit R, a reaction solution setting unit S, two mixing units M, an extracting and separating unit E, an upper layered isolate collection unit U and a lower layered isolate collection unit L. The difference between the second type of continuous reactor and the first type of continuous reactor is that the reaction solution is fed in stages to react with the reactant; specifically, when the reactant is transported to a first mixing unit M, one part of the reaction solution in the reaction solution setting unit S will be first transported to the first mixing unit M for performing a first mixing reaction, and then, the other part of the reaction solution in the reaction solution setting unit S will be transported to a second mixing unit M for performing a second mixing reaction, that is, the reaction solution will be reacted with the reactant in stages, and finally, the mixed reaction solution and the reactant will be separated by the extracting and separating unit E; further, the second type of continuous reactor can have more mixing units M disposed as needed (two are shown in FIG. 2, but more can be added), and the number of the mixing units are not limited by the present invention. The method of the present invention can combine the first type and the second type of continuous reactors as needed to perform the cleaning step (b) and the extracting step (c).

The first embodiment of the method of the present invention for purifying a polyunsaturated fatty acid by using a continuous reactor is performed by using the first type of continuous reactor as shown in FIG. 1. In this embodiment, the method of the present invention comprises, in sequence, a complexing step (a), a cleaning step (b), an extracting step (c) and a concentrating and drying step (d). In the complexing step (a), the reactant setting unit R and the reaction solution setting unit S of the first type of continuous reactor are respectively configured to set a polyunsaturated fatty acid as a reactant and set a silver salt aqueous solution as a reaction solution, and the polyunsaturated fatty acid and the silver salt aqueous solution are transported by the pump P to the mixing unit M and reacted in the mixing unit M, and then separated into a first aqueous layer and an oil layer by using the extracting and separating unit E, wherein the first aqueous layer is collected to the lower layered isolate collection unit L while the oil layer is collected to the upper layered isolate collection unit U. In the cleaning step (b), the reactant setting unit R and the reaction solution setting unit S of the first type of continuous reactor are respectively configured to set the first aqueous layer as a reactant and set a first organic solvent as a reaction solution, and the first aqueous layer and the first organic solvent are transported by the pump P to the mixing unit M and reacted in the mixing unit M, and then separated into a second aqueous layer and a first organic layer by using the extracting and separating unit E after the reaction. In the extracting step (c), the reactant setting unit R and the reaction solution setting unit S of the first type of continuous reactor are respectively configured to set the second aqueous layer as a reactant and set a second organic solvent as a reaction solution, and the second aqueous layer and the second organic solvent are transported by the pump P to the mixing unit M and reacted in the mixing unit M, and then separated into a third aqueous layer and a second organic layer by using the extracting and separating unit E after the reaction. Finally, in the concentrating and drying step (d), the second organic layer is concentrated and dried so as to obtain a purified polyunsaturated fatty acid.

The second embodiment of the method of the present invention for purifying a polyunsaturated fatty acid by using a continuous reactor is performed by using the first type of continuous reactor together with the second type of continuous reactor as shown in FIG. 1 and FIG. 2. In this embodiment, the method of the present invention comprises, in sequence, a complexing step (a), a cleaning step (b), an extracting step (c) and a concentrating and drying step (d). In the complexing step (a), the reactant setting unit R and the reaction solution setting unit S of the first type of continuous reactor are respectively configured to set a polyunsaturated fatty acid as a reactant and set a silver salt aqueous solution as a reaction solution, and the polyunsaturated fatty acid and the silver salt aqueous solution are transported by the pump P to the mixing unit M and reacted in the mixing unit M, and then separated into a first aqueous layer and an oil layer by using the extracting and separating unit E, wherein the first aqueous layer is collected to the lower layered isolate collection unit L while the oil layer is collected to the upper layered isolate collection unit U. In the cleaning step (b), the reactant setting unit R and the reaction solution setting unit S of the second type of continuous reactor are respectively configured to set the first aqueous layer as a reactant and set a first organic solvent as a reaction solution, and the first aqueous layer and the first organic solvent are transported by the pump P to the mixing unit M and reacted in the mixing unit M, and then separated into a second aqueous layer and a first organic layer by using the extracting and separating unit E after the reaction. In the extracting step (c), the reactant setting unit R and the reaction solution setting unit S of the second type of continuous reactor are respectively configured to set the second aqueous layer as a reactant and set a second organic solvent as a reaction solution, and the second aqueous layer and the second organic solvent are transported by the pump P to the mixing unit M and reacted in the mixing unit M, and then separated into a third aqueous layer and a second organic layer by using the extracting and separating unit E after the reaction. Finally, in the concentrating and drying step (d), the second organic layer is concentrated and dried so as to obtain a purified polyunsaturated fatty acid.

In the method of the present invention, preferably, in the complexing step (a), the polyunsaturated fatty acid may be added with a first organic solvent, and the weight ratio of the first organic solvent and the polyunsaturated fatty acid is 1:20 to 1:1, preferably 1:2 to 1:1, wherein the first organic solvent is preferably n-heptane.

In the method of the present invention, the cleaning step (b) can be performed at least once as needed. When the cleaning step (b) is performed more than once, the aqueous layer obtained last time is used as the second aqueous layer to be processed by the extracting step (c). For example, when the second cleaning step (b) begins to be performed after the first cleaning step (b) is completed, the second aqueous layer obtained by the first cleaning step (b) will be used as the first aqueous layer and re-enter the mixing unit M to react with the first organic solvent, and then the reacted product of the first aqueous layer and the first organic solvent is separated by the extracting and separating unit E into the second aqueous layer and the first organic layer, and the second aqueous layer obtained secondly will be processed by the extracting step (c). In addition, the different cleaning steps (b) can use different types of continuous reactors; for example, the first cleaning step (b) can use the first type of continuous reactor, and the second cleaning step (b) can use the second type of continuous reactor.

In the method of the present invention, the extracting step (c) can be performed at least once as needed. When the extracting step (c) is performed more than once, the second organic layers obtained every time will be combined and collected and used as the second organic layer to be processed by the concentrating and drying step (d). For example, when the second extracting step (c) begins to be performed after the first extracting step (c) is completed, the third aqueous layer obtained by the first extracting step (c) is used as the second aqueous layer and re-enters the mixing unit M to react with the second organic solvent, and the reacted product of the third aqueous layer and the second organic solvent is separated by the extracting and separating unit E into the third aqueous layer and the second organic layer, and then the second organic layer obtained by the first extracting step (c) and the second organic layer obtained by the second extracting step (c) are combined and collected as the second organic layer to be processed by the concentrating and drying step (d). In addition, the different extracting steps (c) can use different types of continuous reactors; for example, the first extracting step (c) can use the first type of continuous reactor, and the second extracting step (c) can use the second type of continuous reactor. Preferably, before the extracting step (c) is performed, the second aqueous layer can be extracted after being diluted with pure water, which can increase the volume of the second aqueous layer, so as to increase the volume of the third aqueous layer after the extraction and recycle the silver salt aqueous solution in the third aqueous layer, wherein the weight of the pure water for dilution may be 1 to 10 times the weight of the polyunsaturated fatty acid, such as 1 time, 2 times, 3 times, 4 times, 5 times, 6 times, 7 times, 8 times, 9 times or 10 times, and preferably 10 times.

In the method of the present invention, the second organic layer can further be cleaned with water and saturated saline before being concentrated in the step (d), and then activated carbon (used for decoloration) is added into the second organic layer, which is then stirred and filtered.

The method of the present invention is performed under light avoidance and inert gas conditions, wherein the inert gas is preferably nitrogen.

In the method of the present invention, the silver salt of the silver salt aqueous solution A refers to any silver salt that can form a complex with an unsaturated chain end and is usually a silver compound, such as silver nitrate, silver perchlorate, silver acetate, silver tetrafluoroborate or any of their combination, which is soluble in an aqueous substance. The aqueous substance refers to water and compounds with hydroxyl groups, e.g., glycerol, ethylene glycol or any of their combination. In this disclosure, the concentration of the silver salt is 40~80 wt % or more, such as 40 wt %, 45 wt %, 50 wt %, 55 wt %, 60 wt %, 65 wt %, 70 wt %, 75 wt % or 80 wt %, of which 60~75 wt % is preferred. The polyunsaturated fatty acid must be in the form of a complex so as to facilitate its distribution in an aqueous layer. Therefore, if the concentration of the silver salt aqueous solution is insufficient, i.e., below the above-mentioned range, the amount of the complex formed is too small, resulting in that the amount of the polyunsaturated fatty acid dissolved in the aqueous layer will also be too small, which will affect the amount of the polyunsaturated fatty acid that can be purified.

In the method of the present invention, the polyunsaturated fatty acid comprises eicosatetraenoic acid (ETA), eicosatetraenoic acid ethyl ester, eicosapentaenoic acid (EPA), eicosapentaenoic acid ethyl ester (EPAE), heneicosapentaenoic acid (HPA), heneicosapentaenoic acid ethyl ester, docosapentaenoic acid (DPA), docosapentaenoic acid ethyl ester, docosahexaenoic acid (DHA), docosahexaenoic acid ethyl ester (DHAEE), tetracosapentaenoic acid, tetracosapentaenoic acid ethyl ester, nisinic acid or nisinic acid ethyl ester, and the present invention is not limited to these, wherein the purity of the polyunsaturated fatty acid is preferably 60% or more.

In the method of the present invention, the first organic solvent and the second organic solvent include hexane, cyclohexane, heptane, n-heptane, toluene, ethyl acetate, ethyl isopropionate, xylene, ethylbenzene, methylene chloride, methyl tert-butyl ether, tetrahydrofuran (THF), 2-methyltetrahydrofuran, ethyl ether, dipropyl ether or isopropyl ether, and the present invention is not limited thereto, wherein the first organic solvent is preferably heptane or n-heptane, and the second organic solvent is preferably toluene.

In general, the purification standard of the purified polyunsaturated fatty acid is above 96.5%, and each single impurity must be ≤0.40%. The polyunsaturated fatty acid obtained by the method of the present invention can reach more than 98%, which meets the purification standard.

EMBODIMENTS

Hereinafter, the present invention will be further described with detailed description and embodiments. However, it should be understood that these embodiments are only used to facilitate easier understanding of the present invention and not to limit the scope of the invention.

In the following embodiments and test examples, the polyunsaturated fatty acid used is eicosapentaenoic acid ethyl ester (EPAE) (EPAE-70; brand: CCSB; and its purity is more than 65%).

In the following embodiments and test examples, the purity was tested and obtained by using a gas chromatography flame ionization detector (GC-FID) under the following test conditions:
  Instrument: Agilent 6890N/7890A gas chromatography instrument with a flame ionization detector.
  Separation tubular column: capillary gas chromatography column (brand: Supelcowax; 30 m×0.25 mm ID, 0.25 µm).
  Flow velocity: 1 mL/min (helium).
  Injection temperature: 250° C.
  Column temperature: initial temperature is 170° C. maintained for 2 minutes, and then it is increased to 240° C. at a rate of 3° C. per minute and maintained for 9.67 minutes.
  Detector temperature: 270° C.
  Injection sample volume: 1.0 µL.
  Split ratio: 1:200.

Test Example I—Test the Effect of Concentration of Silver Salt Aqueous Solution on Yield and Purity The following test example is to test the effect of different concentrations of silver salt aqueous solution on a purified polyunsaturated fatty acid, and this test example uses a traditional stirring method for performing compound reaction.

Test Example 1

16.88 g of silver nitrate and 7 mL of pure water are used to form 71 wt % of silver nitrate aqueous solution, and 10 g of EPAE-70 is added. The silver nitrate aqueous solution is stirred at a room temperature and under nitrogen for 2 hours, and an aqueous layer is extracted after the silver nitrate aqueous solution is left still to form separate layers. After 50 mL of heptane is added to the aqueous layer, two extractions are performed, and the aqueous layer is extracted after it is left still to form separate layers. After 50 mL of pure water is added to the aqueous layer, the aqueous layer is stirred at a room temperature for 1 hour, and then 50 mL of heptane is added followed by two extractions performed, and finally, an organic layer is extracted and combined. After water and saturated saline are used respectively to clean the organic layer, the organic layer is further concentrated to obtain a purified EPAE, which is 3.47 g in total, with a yield that is 34.7% and a purity that is 98.36%.

Test Example 2

This example uses the same method as Test Example 1 to obtain a purified EPAE. The only difference is that 68 wt % of silver nitrate aqueous solution is used (that is, the solution is formed with 16.88 g of silver nitrate and 8 mL of pure water used). The purified EPAE obtained is 3.54 g in total, with a yield that is 35.4% and a purity that is 98.54%.

Test Example 3

This example uses the same method as Test Example 1 to obtain a purified EPAE. The only difference is that 67 wt % of silver nitrate aqueous solution is used (that is, the solution is formed with 16.88 g of silver nitrate and 8.5 mL of pure water used). The purified EPAE obtained is 3.33 g in total, with a yield that is 33.3% and a purity that is 98.36%.

Test Example 4

This example uses the same method as Test Example 1 to obtain a purified EPAE. The only difference is that 65 wt % of silver nitrate aqueous solution is used (that is, the solution is formed with 16.88 g of silver nitrate and 9 mL of pure water used). The purified EPAE obtained is 3.15 g in total, with a yield that is 31.5% and a purity that is 98.62%.

Test Example 5

This example uses the same method as Test Example 1 to obtain a purified EPAE. The only difference is that 63 wt % of silver nitrate aqueous solution is used (that is, the solution is formed with 16.88 g of silver nitrate and 10 mL of pure water used). The purified EPAE obtained is 2.93 g in total, with a yield that is 29.3% and a purity that is 98.56%.

Test Example 6

This example uses the same method as Test Example 1 to obtain a purified EPAE. The only difference is that 63 wt % of silver nitrate aqueous solution is used (that is, the solution is formed with 16.88 g of silver nitrate and 10 mL of pure water used). The purified EPAE obtained is 3.02 g in total, with a yield that is 30.2% and a purity that is 98.62%.

Test Example 7

This example uses the same method as Test Example 1 to obtain a purified EPAE. The only difference is that 51 wt % of silver nitrate aqueous solution is used (that is, the solution is formed with 16.88 g of silver nitrate and 16 mL of pure water used). The purified EPAE obtained is 1.95 g in total, with a yield that is 19.5% and a purity that is 98.74%.

Test Example 8

This example uses the same method as Test Example 1 to obtain a purified EPAE. The only difference is that 40 wt % of silver nitrate aqueous solution is used (that is, the solution is formed with 16.88 g of silver nitrate and 25.3 mL of pure water used). The purified EPAE obtained is 0.74 g in total, with a yield that is 7.4% and a purity that is 98.58%.

TABLE 1

|  | Silver nitrate concentration (wt %) | Yield (%) | Purity (%) |
| --- | --- | --- | --- |
| Test Example 1 | 71 | 34.7 | 98.36 |
| Test Example 2 | 68 | 35.4 | 98.54 |
| Test Example 3 | 67 | 33.3 | 98.36 |
| Test Example 4 | 65 | 31.5 | 98.62 |
| Test Example 5 | 63 | 29.3 | 98.56 |
| Test Example 6 | 63 | 30.2 | 98.62 |
| Test Example 7 | 51 | 19.5 | 98.74 |
| Test Example 8 | 40 | 7.4 | 98.58 |

Embodiment 1

This embodiment uses a micro flow channel mixer device as a continuous reactor, the architecture of which is the same as that shown in FIG. 1. The reactant setting unit R, the reaction solution setting unit S, the upper layered isolate collection unit U and the lower layered isolate collection unit L are brown serum bottles; the mixing unit M is a micro flow channel mixer; the extracting and separating unit E may be a micro extracting separator; and the pump P is an electromagnetic pump. The reaction environment of the micro flow channel mixer is set at 22° C. with nitrogen used and light avoided.

Complexing step (a): As shown in FIG. 1, 354 g of EPAE-70 and 68% of silver nitrate aqueous solution (formed by 600 g of silver nitrate and 285 g of pure water) are respectively set in brown transparent serum bottles (i.e., the reactant setting unit R and the reaction solution setting unit S) and transported by the electromagnetic pump (i.e., the pump P) to the micro flow channel mixer (i.e., the mixing unit M). The EPAE-70 is transported to the micro flow channel mixer at a flow rate of approximately 10 mL/min, and the silver nitrate aqueous solution is transported to the micro flow channel mixer at a flow rate of approximately 11.9 mL/min. After the EPAE-70 and the silver nitrate aqueous solution enter the micro flow channel mixer to react and form a complex (i.e., $Ag^+EPAE$), the complex will enter a micro extracting separator (i.e., the extracting and separating unit E) to be separated into an upper layer and a lower layer, which are then collected respectively with brown transparent serum bottles (i.e., the upper layered isolate collection unit U and the lower layered isolate collection unit L). The upper layer is an oil layer, which is 133 g in total, wherein the purity of EPAE is 32.82%; and the lower layer is a first aqueous layer, which is 1094 g in total, wherein the purity of EPAE is 94.37%. The whole complexing step (a) takes 35 minutes and 20 seconds.

Cleaning step (b): As shown in FIG. 1, the 1094 g of first aqueous layer obtained in the step (a) and 1215 g of n-heptane (i.e., a first organic solvent) are respectively set in brown transparent serum bottles (i.e., the reactant setting unit R and the reaction solution setting unit S) and transported by the electromagnetic pump (i.e., the pump P) to the micro flow channel mixer (i.e., the mixing unit M). The first aqueous layer is transported to the micro flow channel mixer at a flow rate of approximately 16.8 mL/min, and the n-heptane is transported to the micro flow channel mixer at a flow rate of approximately 40.2 mL/min. After the first aqueous layer and the n-heptane enter the micro flow channel mixer, the n-heptane is reacted to clean the first aqueous layer, and then they will enter the micro extracting separator (i.e., the extracting and separating unit E) to be separated into an upper layer and a lower layer, which are then collected respectively with brown transparent serum bottles (i.e., the upper layered isolate collection unit U and the lower layered isolate collection unit L). The upper layer is an n-heptane layer, which is 1269 g in total, wherein the purity of EPAE is 83.77%; and the lower layer is a cleaned aqueous layer, which is 1025 g in total, wherein the purity of EPAE is 97.75%. Afterwards, a second cleaning step (b) is performed, wherein the 1025 g of cleaned aqueous layer obtained in the first cleaning step (b) and 1215 g of n-heptane (i.e., a first organic solvent) are respectively set in brown transparent serum bottles (i.e., the reactant setting unit R and the reaction solution setting unit S) and transported by the electromagnetic pump to the micro flow channel mixer. The cleaned aqueous layer is transported to the micro flow channel mixer at a flow rate of approximately 17.8 mL/min, and the n-heptane is transported to the micro flow channel mixer at a flow rate of approximately 46.9 mL/min. After the cleaned aqueous layer and the n-heptane enter the micro flow channel mixer, the n-heptane is reacted to clean the cleaned aqueous layer, and then they will enter the micro extracting separator to be separated into an upper layer and a lower layer, which are then collected respectively with brown transparent serum bottles (i.e., the reactant setting unit R and the reaction solution setting unit S). The upper layer (i.e., a first organic layer) is an n-heptane layer, which is 1252 g in total, wherein the purity of EPAE is 92.52%; and the lower layer is a second cleaned aqueous layer (i.e., a second aqueous layer), which is 988 g in total, wherein the purity of EPAE is 98.32%. The first cleaning step (b) takes 43 minutes and 30 seconds, and the second cleaning step (b) takes 37 minutes and 20 seconds.

Extracting step (c): As shown in FIG. 1, the 988 g of second aqueous layer obtained in the step (b) and 3398 g of toluene (i.e., a second organic solvent) are respectively set in brown transparent serum bottles (i.e., the reactant setting unit R and the reaction solution setting unit S) and transported by the electromagnetic pump (i.e., the pump P) to the micro flow channel mixer (i.e., the mixing unit M). The second aqueous layer is transported to the micro flow channel mixer at a flow rate of approximately 14.2 mL/min, and the toluene is transported to the micro flow channel mixer at a flow rate of approximately 73.5 mL/min. After the second aqueous layer and the toluene enter the micro flow channel mixer, the toluene is reacted to extract a complex ($Ag^+EPAE$) of the second aqueous layer, and then they will enter the micro extracting separator (i.e., the extracting and separating unit E) to be separated into an upper layer and a lower layer, which are then collected respectively with brown transparent serum bottles (i.e., the upper layered isolate collection unit U and the lower layered isolate collection unit L). The upper layer is a toluene layer (i.e., a second organic layer), which is 3437 g in total, wherein the purity of EPAE is 97.86%; and the lower layer is a first extracted aqueous layer, which is 914 g in total, wherein the purity of EPAE is 98.72%. Afterwards, a second extracting step (c) is performed, wherein the 914 g of first extracted aqueous layer and 3398 g of toluene (i.e., a second organic solvent) are respectively set in brown transparent serum bottles (i.e., the reactant setting unit R and the reaction solution setting unit S) and transported by the electromagnetic pump to the micro flow channel mixer. The first extracted aqueous layer is transported to the micro flow channel mixer at a flow rate of approximately 13.4 mL/min, and the toluene is transported to the micro flow channel mixer at a flow rate of approximately 79.9 mL/min. After the first extracted aqueous layer and the toluene enter the micro flow channel mixer, the toluene is reacted to extract a complex ($Ag^+EPAE$) of the first extracted aqueous layer, and then they will enter the micro extracting separator to be separated into an upper layer and a lower layer, which are then collected respectively with brown transparent serum bottles (i.e., the upper layered isolate collection unit U and the lower layered isolate collection unit L). The upper layer (i.e., a second organic layer) is a toluene layer, which is 3462 g in total, wherein the purity of EPAE is 98.63%; and the lower layer is a second extracted aqueous layer (i.e., a third aqueous layer), which is 858 g in total, wherein the purity of EPAE is 98.37%. The first extracting step (c) takes 46 minutes and 0 seconds, and the second extracting step (c) takes 42 minutes and 30 seconds.

Concentrating and drying step (d): The toluene layers (i.e., the second organic layers) obtained by the two extractions performed in the step (c) are combined as one toluene layer with a weight that is 6899 g (i.e., 3437 g and 3462 g) and with 1770 g of pure water added, and the one toluene layer is set into a 30 L reaction kettle, stirred for 15 minutes and left still for another 15 minutes, wherein the upper layer is a toluene layer; 3430 g of saline is then added to the one toluene layer, which is then stirred for 15 minutes and left still for another 15 minutes; afterwards, an upper layer that is an toluene layer is then collected and concentrated to 111.83 g; next, 500 mL of n-heptane (i.e., the first organic solvent) and 5 g of activated carbon are added to the concentrated toluene layer, which is then stirred for 15 minutes, filtered, concentrated and dried to obtain a purified EPAE, which is 93.25 g in total, with a yield that is 26.34% and a purity that is 98.17%.

Embodiment 2

This embodiment uses two types of micro flow channel mixer devices as continuous reactors, the architectures of which are the same as that shown in FIGS. 1 and 2. The reactant setting unit R, the reaction solution setting unit S, the upper layered isolate collection unit U and the lower layered isolate collection unit L are brown serum bottles; the mixing unit M is a micro flow channel mixer; the extracting and separating unit E may be a micro extracting separator; and the pump P is an electromagnetic pump. The reaction environment of the micro flow channel mixers is set at 22° C. with nitrogen used and light avoided.

Complexing step (a): As shown in FIG. 1, 354 g of EPAE-70 and 68% of silver nitrate aqueous solution (formed by 600 g of silver nitrate and 285 g of pure water) are respectively set in brown transparent serum bottles (i.e., the reactant setting unit R and the reaction solution setting unit S) and transported by the electromagnetic pump (i.e., the pump P) to the micro flow channel mixer (i.e., the mixing unit M). The EPAE-70 is transported to the micro flow channel mixer at a flow rate of approximately 10.7 mL/min, and the silver nitrate aqueous solution is transported to the micro flow channel mixer at a flow rate of approximately 11.0 mL/min. After the EPAE-70 and the silver nitrate aqueous solution enter the micro flow channel mixer to react and form a complex (i.e., $Ag^+EPAE$), the complex will enter the micro extracting separator (i.e., the extracting and separating unit E) to be separated into an upper layer and a lower layer, which are then collected respectively with brown transparent serum bottles (i.e., the upper layered isolate collection unit U and the lower layered isolate collection unit L). The upper layer is an oil layer, which is 139 g in total, wherein the purity of EPAE is 35.0%; and the lower layer is an aqueous layer (i.e., a first aqueous layer), which is 1087 g in total, wherein the purity of EPAE is 93.80%. The whole complexing step (a) takes 37 minutes and 20 seconds.

Cleaning step (b): As shown in FIG. 2, the 1087 g of first aqueous layer obtained in the step (a) and 1289 g of n-heptane (i.e., a first organic solvent) are respectively set in brown transparent serum bottles (i.e., the reactant setting unit R and the reaction solution setting unit S). The first aqueous layer is transported to a first micro flow channel mixer (i.e., a mixing unit M) at a flow rate of approximately 15.3 mL/min, and at the same time, the n-heptane is transported and fed, in stages, into the first micro flow channel mixer and a second micro flow channel mixer (i.e., a mixing unit M) at a flow rate of approximately 44.5 mL/min. When the first aqueous layer and the n-heptane enter the first micro flow channel mixer and the second micro flow channel mixer, the n-heptane is reacted to clean the first aqueous layer, and then they will enter a micro extracting separator (i.e., the extracting and separating unit E) to be separated into an upper layer and a lower layer, which are then collected respectively with brown transparent serum bottles (i.e., the upper layered isolate collection unit U and the lower layered isolate collection unit L). Only one cleaning process is performed, and the upper layer is an n-heptane layer (i.e., a first organic layer), which is 1361 g in total, wherein the purity of EPAE is 83.00%; and the lower layer is a cleaned aqueous layer (i.e., a second aqueous layer), which is 1012 g in total, wherein the purity of EPAE is 97.91%. The whole cleaning step (b) takes 41 minutes and 50 seconds.

Extracting step (c): As shown in FIG. 2, the 1012 g of second aqueous layer obtained in the step (b) and 2470 g of toluene (i.e., a second organic solvent) are respectively set in brown transparent serum bottles (i.e., the reactant setting unit R and the reaction solution setting unit S). The second aqueous layer is transported to the first micro flow channel mixer (i.e., a mixing unit M) at a flow rate of approximately 16.0 mL/min, and at the same time, the toluene is transported and fed, in stages, into the first micro flow channel mixer and the second micro flow channel mixer (i.e., a mixing unit M) at a flow rate of approximately 76.0 mL/min. After the second aqueous layer and the toluene enter the first micro flow channel mixer and the second micro flow channel mixer, they will then enter a micro extracting separator to be separated into an upper layer and a lower layer, which are then collected respectively with brown transparent serum bottles (i.e., the upper layered isolate collection unit U and the lower layered isolate collection unit L). The upper layer is a toluene layer (i.e., a second organic layer), which is 2534 g in total, wherein the purity of EPAE is 97.36%; and the lower layer is a first extracted aqueous layer, which is 925 g in total, wherein the purity of EPAE is 98.72%. Afterwards, a second extracting step (c) is performed, wherein the 925 g of first extracted aqueous layer and 2170 g of toluene (i.e., a second organic solvent) are respectively set in brown transparent serum bottles. The first extracted aqueous layer is transported to the first micro flow channel mixer at a flow rate of approximately 17.9 mL/min, and at the same time, the toluene is transported and fed, in stages, into the first micro flow channel mixer and the second micro flow channel mixer at a flow rate of approximately 82.0 mL/min. After the first extracted aqueous layer and the toluene enter the first micro flow channel mixer and the second micro flow channel mixer, they will then enter the micro extracting separator to be separated into an upper layer and a lower layer, which are then collected respectively with brown transparent serum bottles (i.e., the upper layered isolate collection unit U and the lower layered isolate collection unit L). The upper layer (i.e., a second organic layer) is a toluene layer, which is 2125 g in total, wherein the purity of EPAE is 98.91%; and the lower layer is a second extracted aqueous layer (i.e., a third aqueous layer), which is 874 g in total, wherein the purity of EPAE is 98.46%. The first extracting step (c) takes 37 minutes and 30 seconds, and the second extracting step (c) takes 30 minutes and 30 seconds.

Concentrating and drying step (d): The toluene layers (i.e., the second organic layers) obtained by the two extractions performed in the step (c) are combined as one toluene layer with a weight that is 4659 g (i.e., 2534 g and 2125 g) and with 1770 g of pure water added, and the one toluene layer is set into a 30 L reaction kettle, stirred for 15 minutes and left still for another 15 minutes, wherein the upper layer is a toluene layer; 3430 g of saline is then added to the one toluene layer, which is then stirred for 15 minutes and left still for another 15 minutes; afterwards, an upper layer that is an toluene layer is then collected; next, 500 mL of n-heptane (i.e., the first organic solvent) and 5 g of activated carbon are added to the collected toluene layer, which is then stirred for 15 minutes, filtered, concentrated and dried to obtain a purified EPAE, which is 97.63 g in total, with a yield that is 27.62% and a purity that is 97.62%.

Test Example II—Test the Effect of Adding Different Ratios of the First Organic Solvent on the Extraction Efficiency and Purity of Polyunsaturated Fatty Acid and Silver Nitrate Aqueous Solution The following test examples 9 to 15 are to test the effect of adding different ratios of the first organic solvent (i.e., n-heptane) on the extraction efficiency and purity of polyunsaturated fatty acid and silver nitrate aqueous solution. The test examples all include the test condition that 50 g of EPAE-70 and 68% of silver salt aqueous solution are stirred at a room temperature for 2 hours and left still to form separate layers including an aqueous layer and an oil layer, which will then be weighed and analyzed for purity. The test results are shown in Table 2 below, wherein when the weight ratio of n-heptane to EPAE-70 is 50:100 or more, the purity of the purified EPAE-70 in the aqueous layer can be improved. This result shows that, prior to the complexing step (a), adding a significant proportion of the first organic solvent to the polyunsaturated fatty acid can effectively increase the purity of the polyunsaturated fatty acid in the aqueous layer.

TABLE 2

| | Weight ratio of n-heptane and EPAE-70 | Purified EPAE in aqueous layer | | Purified EPAE in the oil layer | |
|---|---|---|---|---|---|
| | | Purity (%) | Weight (g) | Purity (%) | Weight (g) |
| Test Example 9 | 5:100 | 94.743 | 152.45 | 29.22 | 20.39 |
| Test Example 10 | 10:100 | 94.758 | 149.65 | 33.62 | 24.11 |
| Test Example 11 | 20:100 | 95.758 | 148.99 | 34.53 | 29.20 |
| Test Example 12 | 30:100 | 96.350 | 150.78 | 38.98 | 34.74 |
| Test Example 13 | 40:100 | 96.373 | 150.48 | 39.31 | 39.79 |
| Test Example 14 | 50:100 | 96.556 | 149.64 | 40.81 | 44.57 |
| Test Example 15 | 100:100 | 96.979 | 148.25 | 43.52 | 71.40 |

Embodiment 3

This embodiment uses two types of micro flow channel mixer devices as continuous reactors, the architectures of which are the same as that shown in FIGS. 1 and 2. The reactant setting unit R, the reaction solution setting unit S, the upper layered isolate collection unit U and the lower layered isolate collection unit L are brown serum bottles; the mixing unit M is a micro flow channel mixer; the extracting and separating unit E may be a micro extracting separator; and the pump P is an electromagnetic pump. The reaction environment of the micro flow channel mixers is set at 22° C. with nitrogen used and light avoided.

Complexing step (a): As shown in FIG. 1, EPAE-70 containing n-heptane (n-heptane is 177 g, EPAE-70 is 354 g; the weight ratio of n-heptane and EPAE-70 is 50:100) and 68% of silver nitrate aqueous solution (formed by 600 g of silver nitrate and 285 g of pure water) are respectively set in brown transparent serum bottles (i.e., the reactant setting unit R and the reaction solution setting unit S) and transported by the electromagnetic pump (i.e., the pump P) to the micro flow channel mixer (i.e., the mixing unit M). The EPAE-70 containing n-heptane and the silver nitrate aqueous solution will be transported to the micro flow channel mixer after their flow rates are set. After the EPAE-70 containing n-heptane and the silver nitrate aqueous solution enter the micro flow channel mixer to react and form a complex (i.e., Ag$^+$EPAE), the complex will enter a micro extracting separator (i.e., the extracting and separating unit E) to be separated into an upper layer and a lower layer, which are then collected respectively with brown transparent serum bottles (i.e., the upper layered isolate collection unit U and the lower layered isolate collection unit L). The upper layer is an oil layer, which is 176 g in total, wherein the purity of EPAE is 49.40%; and the lower layer is an aqueous layer (i.e., a first aqueous layer), which is 1009 g in total, wherein the purity of EPAE is 96.45%. The whole complexing step (a) takes 21 minutes and 5 seconds.

Cleaning step (b): As shown in FIG. 1, the 1009 g of aqueous layer (i.e. first aqueous layer) obtained in the step (a) and 408 g of n-heptane (i.e., a first organic solvent) are respectively set in brown transparent serum bottles (i.e., the reactant setting unit R and the reaction solution setting unit S) and transported by the electromagnetic pump (i.e., the pump P) to the micro flow channel mixer (i.e., the mixing unit M). The first aqueous layer is transported to the micro flow channel mixer at a flow rate of approximately 28.8 mL/min, and the n-heptane is transported to the micro flow channel mixer at a flow rate of approximately 27.8 mL/min. After the first aqueous layer and the n-heptane enter the micro flow channel mixer, the n-heptane is reacted to clean the first aqueous layer, and then they will enter the micro extracting separator (i.e., the extracting and separating unit E) to be separated into an upper layer and a lower layer, which are then collected respectively with brown transparent serum bottles (i.e., the upper layered isolate collection unit U and the lower layered isolate collection unit L). The upper layer is an n-heptane layer, which is 424 g in total, wherein the purity of EPAE is 90.47%; and the lower layer is a cleaned aqueous layer, which is 977 g in total, wherein the purity of EPAE is 98.09%. Afterwards, a second cleaning step (b) is performed, wherein the 977 g of cleaned aqueous layer and 408 g of n-heptane (i.e., a first organic solvent) are respectively set in brown transparent serum bottles (i.e., the reactant setting unit R and the reaction solution setting unit S) and transported by the electromagnetic pump to the micro flow channel mixer. The cleaned aqueous layer is transported to the micro flow channel mixer at a flow rate of approximately 23.1 mL/min, and the n-heptane is transported to the micro flow channel mixer at a flow rate of approximately 24.1 mL/min. After the cleaned aqueous layer and the n-heptane enter the micro flow channel mixer, the n-heptane is reacted to clean the cleaned aqueous layer, and then they will enter the micro extracting separator to be separated into an upper layer and a lower layer, which are then collected respectively with brown transparent serum bottles (i.e., the upper layered isolate collection unit U and the lower layered isolate collection unit L). The upper layer is an n-heptane layer (i.e., a first organic layer), which is 413 g in total, wherein the purity of EPAE is 93.79%; and the lower layer is a second cleaned aqueous layer (i.e., a second aqueous layer), which is 949 g in total, wherein the purity of EPAE is 98.45%. The first cleaning step (b) takes 21 minutes and 11 seconds, and the second cleaning step (b) takes 24 minutes and 34 seconds.

Extracting step (c): 3540 g of pure water is added into the 949 g of second aqueous layer obtained in the step (b) to obtain a diluted second aqueous layer. Afterwards, a first extracting step (c) is performed as shown in FIG. 2, wherein the cleaned and diluted second aqueous layer and 240 g of n-heptane (i.e., a second organic solvent) are respectively set in brown transparent serum bottles (i.e., the reactant setting unit R and the reaction solution setting unit S) and transported by the electromagnetic pump (i.e., the pump P) to the micro flow channel mixer (i.e., the mixing unit M). The diluted second aqueous layer is transported to the micro flow channel mixer at a flow rate of approximately 17.7 mL/min, and the n-heptane is transported to the micro flow channel mixer at a flow rate of approximately 7.9 mL/min. After the diluted second aqueous layer and the n-heptane enter the micro flow channel mixer, the n-heptane is reacted to extract a complex ($Ag^+EPAE$) of the diluted second aqueous layer, and then they will enter the micro extracting separator (i.e., the extracting and separating unit E) to be separated into an upper layer and a lower layer, which are then collected respectively with brown transparent serum bottles (i.e., the upper layered isolate collection unit U and the lower layered isolate collection unit L). The upper layer is a n-heptane layer (i.e., a second organic layer), which is 318.2 g, wherein the purity of EPAE is 98.43%; and the lower layer is a first extracted aqueous layer, which is 4274 g, wherein the purity of EPAE is 98.44%. Afterwards, a second extracting step (c) is performed as shown in FIG. 1, wherein the 4274 g of first extracted aqueous layer and 240 g of n-heptane (i.e., a second organic solvent) are respectively set in brown transparent serum bottles (i.e., the reactant setting unit S and the reaction solution setting unit S) and transported by the electromagnetic pump to the micro flow channel mixer. The first extracted aqueous layer is transported to the micro flow channel mixer at a flow rate of approximately 107.3 mL/min, and the n-heptane is transported to the micro flow channel mixer at a flow rate of approximately 6.6 mL/min. After the first extracted aqueous layer and the n-heptane enter the micro flow channel mixer, the n-heptane is reacted to extract a complex ($Ag^+EPAE$) of the first extracted aqueous layer, and then they will enter the micro extracting separator to be separated into an upper layer and a lower layer, which are then collected respectively with brown transparent serum bottles (i.e., the upper layered isolate collection unit U and the lower layered isolate collection unit L). The upper layer is an n-heptane layer (i.e., a second organic layer), which is 239.4 g, wherein the purity of EPAE is 98.41%; and the lower layer is a second extracted aqueous layer (i.e., a third aqueous layer), which is 4165 g, wherein the purity of EPAE is 99.10%. The first extracting step (c) takes 30 minutes and 25 seconds, and the second extracting step (c) takes 36 minutes and 12 seconds.

Concentrating and drying step (d): The n-heptane layers (i.e., the second organic layers) obtained by the two extractions performed in the step (c) are combined as one layer with a weight that is 557.6 g (i.e., 318.2 g and 239.4 g) and with 1770 g of pure water added, and the one layer is set into a 30 L reaction kettle, stirred for 15 minutes and left still for another 15 minutes, wherein the upper layer is a n-heptane layer; 3430 g of saline is then added to the one layer, which is then stirred for 15 minutes and left still for another 15 minutes; afterwards, an upper layer that is a n-heptane layer is then collected; next, 5 g of activated carbon is added to the n-heptane layer, which is then stirred for 15 minutes, filtered, concentrated and dried to obtain a purified EPAE, which is 110.5 g in total, with a yield that is 31.2% and a purity that is 98.53%.

As shown in Table 3 and Table 4, the purity of the purified EPAEs obtained in embodiments 1 to 3 are 98.17%, 97.62% and 98.53%, respectively, which all achieve a purity of more than 96.5%; in the step (b), the single impurities in the second aqueous layers of embodiments 1 to 3 all reach a percentage that is 0.40%, which shows that the method of the present invention can effectively purify polyunsaturated fatty acid. The embodiment 1 and the embodiment 2 are compared; in the embodiment 2, a second type of continuous reactor is used, a reaction solvent are fed in stages, and the purity of the purified EPAE can reach 96.5% or more, which shows that, compared with the embodiment 1 using the first type of continuous reactor, the embodiment 2 can significantly reduce the amount of the first organic solvent and the second organic solvent used but does not affect the effect of the purified EPAE; that is, the use of the second type of continuous reactor can effectively reduce the amount of the used organic solvent, which is beneficial for the method of the present invention to effectively reduce the amount of organic solvent used in industrial mass production of purified EPAE. The embodiment 3 is compared with the embodiment 1 and the embodiment 2; unlike the embodiment 1 and the embodiment 2, the embodiment 3 has n-heptane added to the polyunsaturated fatty acid before the complexing step (a) and has pure water added to dilute the second aqueous layer before the extracting step (c), the result of which shows that the purity of the purified EPAE in the embodiment 3 is the highest and up to 98.53%, and the amount of the first organic solvent and the second organic solvent used is the least; that is, adding a significant amount of first organic solvent to the polyunsaturated fatty acid before the complexing step (a) can effectively increase the purity of the EPAE in the complexed aqueous layer and reduce the amount of the first organic solvent and the second organic solvent used in the subsequent steps (b) and (c); in addition, the embodiment 3 has pure water added to dilute the second aqueous layer before the extracting step (c), which can not only reduce the amount of the organic solvent used but also increase the volume of the aqueous layer, so as to be beneficial to the recycle of the silver salt aqueous solution in the third aqueous layer after the extracting step.

flow channel mixer can achieve the desired effect regarding the mixing efficiency of the feeding rate ratio of equal or near magnification of the two feeding pumps. However, in the mixing efficiency of the feeding multi-rate ratio (>2), two sets of micro flow channel mixers can be used for feeding in stages to improve the mixing efficiency, and the effect is better. Therefore, the present invention provides a

TABLE 3

|  |  |  | Embodiment 1 | Embodiment 2 | Embodiment 3 |
|---|---|---|---|---|---|
| Step (a) | Polyunsaturated fatty acid solution | EPAE-70 (g) | 354 g | 354 g | 354 g |
|  |  | N-heptane (g) | No addition | No addition | 177 g |
| Step (b) | First cleaning | First organic solvent | N-heptane | N-heptane | N-heptane |
|  |  | Usage amount (g) | 1215 g | 1289 g | 408 g |
|  |  | Times relative of first organic solvent to used amount of EPAE-70 | 3.4 times | 3.6 times | 1.15 times |
|  | Second cleaning | First organic solvent | N-heptane | No second cleaning | N-heptane |
|  |  | Usage amount (g) | 1215 g |  | 408 g |
|  |  | Times relative of first organic solvent to used amount of EPAE-70 | 3.4 times |  | 1.15 times |
|  | Times of total amount of the first organic solvent used in step (b) relative to used amount of EPAE-70 |  | 2430 g | 1289 g | 816 g |
| Before step (c) | Dilute the second aqueous layer with pure water |  | No addition | No addition | Added |
|  | The amount of pure water added |  |  |  | 3540 g |
|  | Times of pure water relative to used amount of EPAE-70 |  |  |  | 10 times |
| Step (c) | First extraction | Second organic solvent | Toluene | Toluene | N-heptane |
|  |  | Usage amount (g) | 3398 g | 2470 g | 240 g |
|  |  | Times of second organic solvent relative to used amount of EPAE-70 | 9.6 times | 6.9 times | 0.68 times |
|  | Second extraction | Second organic solvent | Toluene | Toluene | N-heptane |
|  |  | Usage amount (g) | 3398 g | 2170 g | 240 g |
|  |  | Times of second organic solvent relative to used amount of EPAE-70 | 9.6 times | 6.9 times | 0.68 times |
|  | Times of total amount of the second organic solvent used in step (c) relative to used amount of EPAE-70 |  | 6796 g | 4640 g | 480 g |

TABLE 4

|  |  |  | Embodiment 1 | Embodiment 2 | Embodiment 3 |
|---|---|---|---|---|---|
| Step (a) | Upper layer/oil layer |  | 133 g | 139 g | 176 g |
|  | EPAE purity |  | 32.82% | 35.0% | 49.40% |
|  | Lower layer/first aqueous layer |  | 1094 g | 1087 g | 1009 g |
|  | EPAE purity |  | 94.37% | 93.80% | 96.45% |
| Step (b) | First cleaning | Upper layer/n-heptane layer | 1269 g | 1361 g | 424 g |
|  |  | EPAE purity | 83.77% | 83.00% | 90.47% |
|  |  | Lower layer/cleaned aqueous layer | 1025 g | 1012 g | 977 g |
|  |  | EPAE purity | 97.75% | 97.91% | 98.09% |
|  |  | Single impurity | No test | 0.40% | No test |
|  | Second cleaning | Upper layer/first organic layer | 1252 g | No second cleaning | 413 g |
|  |  | EPAE purity | 92.52% |  | 93.79% |
|  |  | Lower layer/second second aqueous layer | 988 g |  | 949 g |
|  |  | EPAE purity | 98.32% |  | 98.45% |
|  |  | Single impurity | ≤0.40% |  | ≤0.40% |
| Step (c) | First extraction | Upper layer/second organic layer | 3437 g | 2534 g | 318.2 g |
|  |  | EPAE purity | 97.86% | 97.36% | 98.43% |
|  | Second extraction | Upper layer/second organic layer | 3462 g | 2125 g | 239.4 g |
|  |  | EPAE purity | 98.63% | 98.91% | 98.41% |
| Step (d) | Purified EPAE |  |  |  |  |
|  | Yield |  | 93.25 g | 97.63 g | 110.5 g |
|  |  |  | 26.34% | 27.62% | 31.2% |
|  | Purity |  | 98.17% | 97.62% | 98.53% |

Therefore, in the method of the present invention, in order to achieve the best mixing efficiency, using a single micro method for purifying polyunsaturated fatty acid by using a continuous reactor, which provides advantages that the purification process of polyunsaturated fatty acid can be continuously produced, the volume of the reactor can be adjusted according to needs, the process efficiency is high, and the silver salt aqueous solution extracted by the organic solvent can be directly recycled; therefore, the method of the invention is quite competitive.

The above is the detailed description of the present invention. However, the above is merely the preferred embodiment of the invention and cannot be the limitation to the implement scope of the invention, which means the variation and modification according to the present invention may still fall into the scope of the invention.

What is claimed is:

1. A method for purifying polyunsaturated fatty acid using a continuous reactor, which includes a mixing unit and an extracting and separating unit, and the method comprising:
    (a) complexing step: reacting a polyunsaturated fatty acid and a silver salt aqueous solution in the mixing unit, and separating a first aqueous layer and an oil layer using the extracting and separating unit;
    (b) cleaning step: reacting the first aqueous layer and a first organic solvent in the mixing unit, and separating a second aqueous layer and a first organic layer using the extracting and separating unit;
    (c) extracting step: reacting the second aqueous layer and a second organic solvent in the mixing unit, and separating a third aqueous layer and a second organic layer using the extracting and separating unit; and
    (d) concentrating and drying step: concentrating and drying the second organic layer to obtain a purified polyunsaturated fatty acid.

2. A method for purifying polyunsaturated fatty acid using a continuous reactor, which includes a plurality of mixing units and an extracting and separating unit, and the method comprising:
    (a) complexing step: using the plurality of mixing units to react a polyunsaturated fatty acid and a silver salt aqueous solution, and separating a first aqueous layer and an oil layer using the extracting and separating unit;
    (b) cleaning step: a first organic solvent is used to each of the plurality of mixing units in stages, reacting the first aqueous layer and the first organic solvent, and separating a second aqueous layer and a first organic layer using the extracting and separating unit;
    (c) extracting step: a second organic solvent is used to each of the plurality of mixing units in stages, reacting the second aqueous layer and the second organic solvent, and separating a third aqueous layer and a second organic layer using the extracting and separating unit; and
    (d) concentrating and drying step: concentrating and drying the second organic layer to obtain a purified polyunsaturated fatty acid.

3. The method of claim 1, wherein the polyunsaturated fatty acid in the complexing step (a) is added with the first organic solvent, and a weight ratio of the first organic solvent and the polyunsaturated fatty acid is 1:20 to 1:1.

4. The method of claim 2, wherein the polyunsaturated fatty acid in the complexing step (a) is added with the first organic solvent, and a weight ratio of the first organic solvent and the polyunsaturated fatty acid is 1:20 to 1:1.

5. The method of claim 3, wherein the first organic solvent is n-heptane.

6. The method of claim 4, wherein the first organic solvent is n-heptane.

7. The method of claim 1, wherein the second aqueous layer is diluted with pure water before the extracting step (c).

8. The method of claim 2, wherein the second aqueous layer is diluted with pure water before the extracting step (c).

9. The method of claim 1, wherein the second organic layer is further cleaned with water and saturated saline before being concentrated in the step (d).

10. The method of claim 2, wherein the second organic layer is further cleaned with water and saturated saline before being concentrated in the step (d).

11. The method of claim 1, wherein the second organic layer is further added with activated carbon, stirred and filtered after being concentrated and before being dried in the step (d).

12. The method of claim 2, wherein the second organic layer is further added with activated carbon, stirred and filtered after being concentrated and before being dried in the step (d).

13. The method of claim 1, wherein the polyunsaturated fatty acid comprises eicosatetraenoic acid (ETA), eicosatetraenoic acid ethyl ester, eicosapentaenoic acid (EPA), eicosapentaenoic acid ethyl ester (EPAE), heneicosapentaenoic acid (HPA), heneicosapentaenoic acid ethyl ester, docosapentaenoic acid (DPA), docosapentaenoic acid ethyl ester, docosahexaenoic acid (DHA), docosahexaenoic acid ethyl ester (DHAEE), tetracosapentaenoic acid, tetracosapentaenoic acid ethyl ester, nisinic acid or nisinic acid ethyl ester.

14. The method of claim 2, wherein the polyunsaturated fatty acid comprises eicosatetraenoic acid (ETA), eicosatetraenoic acid ethyl ester, eicosapentaenoic acid (EPA), eicosapentaenoic acid ethyl ester (EPAE), heneicosapentaenoic acid (HPA), heneicosapentaenoic acid ethyl ester, docosapentaenoic acid (DPA), docosapentaenoic acid ethyl ester, docosahexaenoic acid (DHA), docosahexaenoic acid ethyl ester (DHAEE), tetracosapentaenoic acid, tetracosapentaenoic acid ethyl ester, nisinic acid or nisinic acid ethyl ester.

15. The method of claim 1, wherein a purity of the polyunsaturated fatty acid of step (a) is 60% or more.

16. The method of claim 2, wherein a purity of the polyunsaturated fatty acid of step (a) is 60% or more.

17. The method of claim 1, wherein a concentration of the silver salt aqueous solution is 40 to 70 wt %.

18. The method of claim 2, wherein a concentration of the silver salt aqueous solution is 40 to 70 wt %.

19. The method of claim 1, wherein the first organic solvent and the second organic solvent include hexane, cyclohexane, heptane, n-heptane, toluene, ethyl acetate, ethyl isopropionate, xylene, ethylbenzene, methylene chloride, methyl tert-butyl ether, tetrahydrofuran (THF), 2-methyltetrahydrofuran, ethyl ether, dipropyl ether or isopropyl ether.

20. The method of claim 2, wherein the first organic solvent and the second organic solvent include hexane, cyclohexane, heptane, n-heptane, toluene, ethyl acetate, ethyl isopropionate, xylene, ethylbenzene, methylene chloride, methyl tert-butyl ether, tetrahydrofuran (THF), 2-methyltetrahydrofuran, ethyl ether, dipropyl ether or isopropyl ether.

21. The method of claim 19, wherein the first organic solvent is heptane or n-heptane.

22. The method of claim 20, wherein the first organic solvent is heptane or n-heptane.

23. The method of claim 19, wherein the second organic solvent is toluene, heptane or n-heptane.

24. The method of claim 20, wherein the second organic solvent is toluene, heptane or n-heptane.

25. The method of claim 1, wherein the mixing unit is a micro flow channel mixer.

26. The method of claim 2, wherein the mixing unit is a micro flow channel mixer.

27. The method of claim 1, wherein the method is performed under light avoidance and inert gas conditions.

28. The method of claim 2, wherein the method is performed under light avoidance and inert gas conditions.

* * * * *